(12) United States Patent
Maury et al.

(10) Patent No.: US 11,359,027 B2
(45) Date of Patent: Jun. 14, 2022

(54) PREVENTION OR TREATMENT OF HEMATOLOGIC MALIGNANCY RELAPSE USING A TNFR2 ANTAGONIST

(71) Applicants: UNIVERSITE PARIS EST CRETEIL VAL DE MARNE, Creteil (FR); INSTITUT NATIONAL DE LA SANTE ET DE LA RECHERCHE MEDICALE (INSERM), Paris (FR); ASSISTANCE PUBLIQUE-HOPITAUX DE PARIS, Paris (FR); SORBONNE UNIVERSITE, Paris (FR); CENTRE NATIONAL DE LA RECHERCHE SCIENTIFIQUE, Paris (FR)

(72) Inventors: Sébastien Maury, Joinville le Pont (FR); José Cohen, Paris (FR); Benoît Salomon, Saint-Maur (FR); Sina Naserian, Saint Maur des Fosses (FR); Mathieu Leclerc, Paris (FR)

(73) Assignees: UNIVERSITE PARIS EST CRETEIL VAL DE MARNE, Creteil (FR); INSTITUT NATIONAL DE LA SANTE ET DE LA RECHERCHE MEDICALE (INSERM), Paris (FR); ASSISTANCE PUBLIQUE—HOPITAUX DE PARIS, Paris (FR); SORBONNE UNIVERSITE, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 300 days.

(21) Appl. No.: 16/312,647

(22) PCT Filed: Jun. 22, 2017

(86) PCT No.: PCT/EP2017/065356
§ 371 (c)(1),
(2) Date: Dec. 21, 2018

(87) PCT Pub. No.: WO2017/220711
PCT Pub. Date: Dec. 28, 2017

(65) Prior Publication Data
US 2019/0330359 A1 Oct. 31, 2019

(30) Foreign Application Priority Data

Jun. 22, 2016 (EP) ..................... 16305754

(51) Int. Cl.
C07K 16/28 (2006.01)
A61K 39/00 (2006.01)
A61P 35/00 (2006.01)
A61K 45/06 (2006.01)

(52) U.S. Cl.
CPC .......... *C07K 16/2878* (2013.01); *A61P 35/00* (2018.01); *A61K 45/06* (2013.01)

(58) Field of Classification Search
CPC ...................... C07K 16/2878; A61K 39/00117
See application file for complete search history.

(56) References Cited

U.S. PATENT DOCUMENTS 10,906,982 B2 * 2/2021 Faustman ............... A61P 43/00
2019/0135929 A1 * 5/2019 Faustman ........... A61K 39/3955

FOREIGN PATENT DOCUMENTS

WO  WO2014124134 A1  8/2014

OTHER PUBLICATIONS

Choi et al (Biol. Blood Marrow Transplant, 2012, 18:1525-1532).*
Kitko et al (Biol. Blood Marrow Transplant, 2016, 22:862-868).*
Govindaraj et al (American Journal of Hematology, 2014, 89:795-802).*
Zheng etal (Blood, 2008, 111:24786-2484).*
Kaymakclan et al (Clinical Immunology, 2009, 131:308-316).*
Kolb (Blood, 20018, 112:4371-4383).*
Gurung, A.B. et al., "Binding of small molecules at interface of protein-protein complex—A newer approach to rational drug design", Saudi Journal of Biological Sciences, (2017), vol. 24, pp. 379-388.
Mukai, Y. et al., "Solution of the Structure of the TNF-TNFR2 Complex", Science Signaling, Nov. 16, 2010, vol. 3, Issue 148, 11 pgs.

* cited by examiner

*Primary Examiner* — Laura B Goddard
(74) *Attorney, Agent, or Firm* — Verrill Dana, LLP

(57) ABSTRACT

The present disclosure relates to the in vivo prevention or treatment of hematologic malignancy relapse using a TNFR2 antagonist (an anti TNFR2 antagonist antibody) (i) for use in the prevention or treatment of hematologic malignancy relapse after allogeneic hematopoietic stem cell transplantation (AHCT) or after a treatment with lymphocytes and (ii) for use in enhancing the graft-versus-leukemia-activity (GVL activity) of a hematopoietic stem cell transplantation (HCT) or a treatment with lymphocytes.

19 Claims, 12 Drawing Sheets

Figure 1:
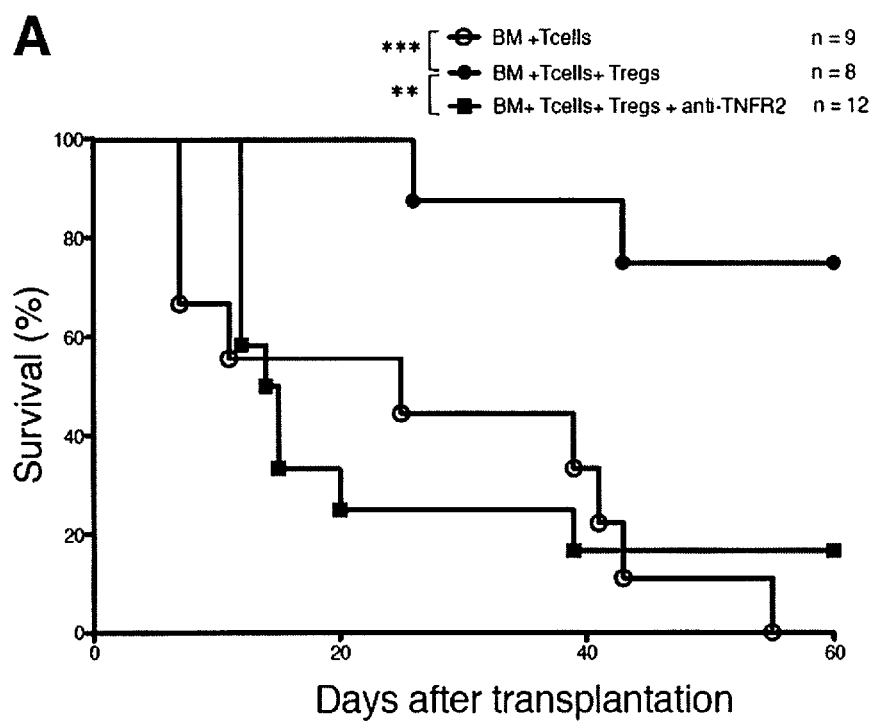
Figure 1:
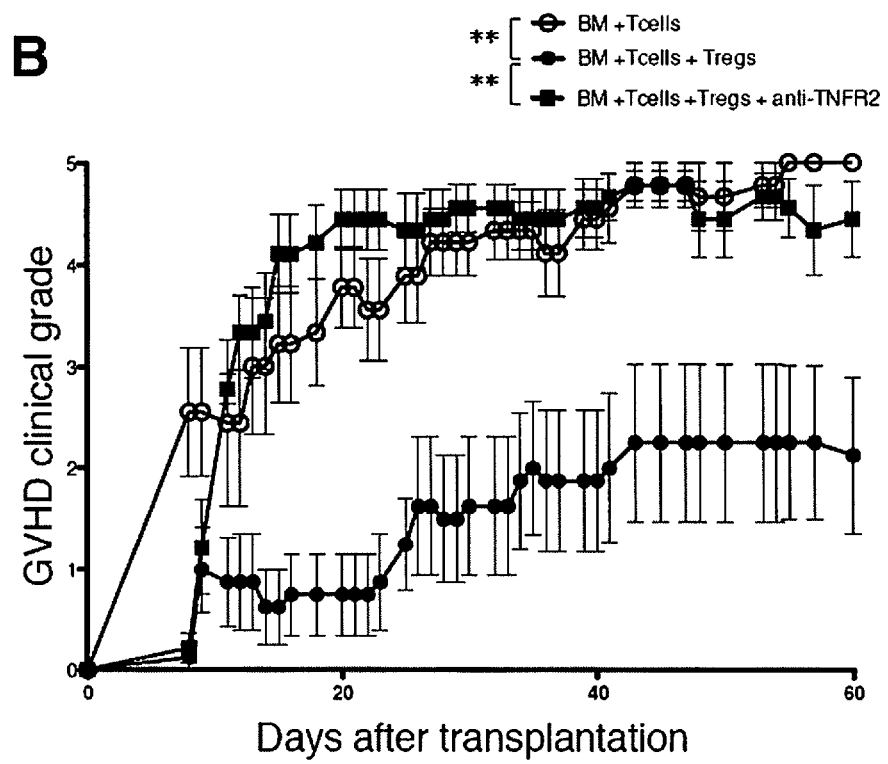
Figure 1:
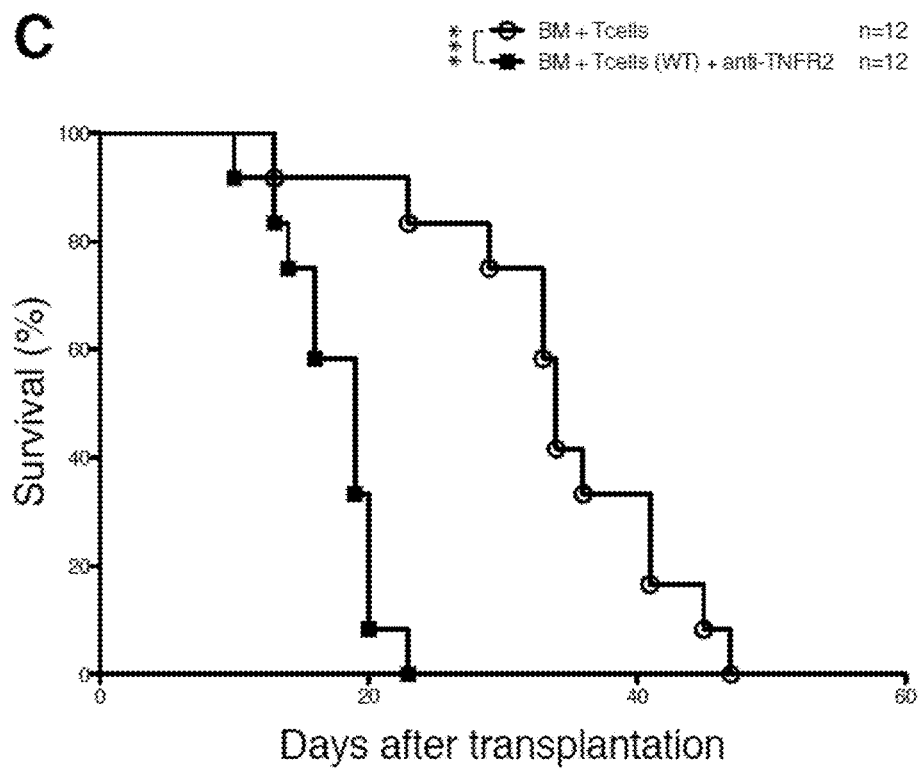
Figure 1:
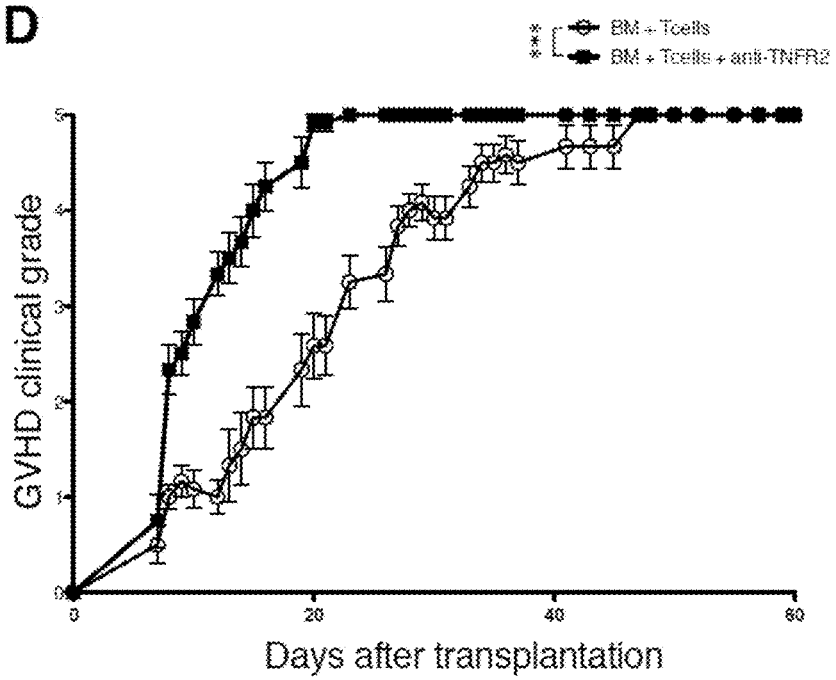

Specification includes a Sequence Listing.

A

B

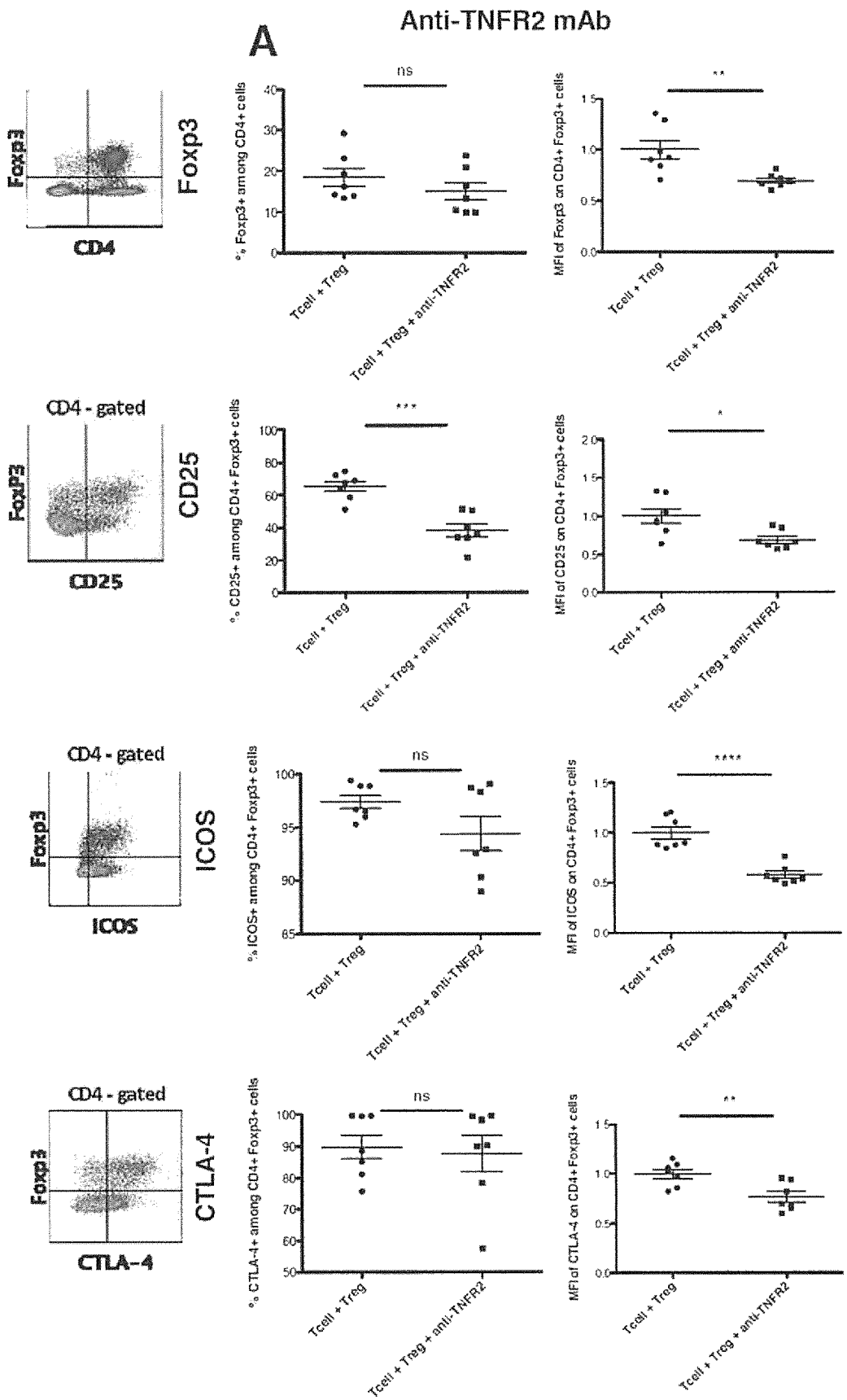

SEQUENCE LISTING

```
<160> NUMBER OF SEQ ID NOS: 1

<210> SEQ ID NO 1
<211> LENGTH: 461
<212> TYPE: PRT
<213> ORGANISM: Homo sapiens

<400> SEQUENCE: 1

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
```

-continued

```
                195                 200                 205
Met Ala Pro Gly Ala Val His Leu Pro Gln Pro Val Ser Thr Arg Ser
        210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Gly Leu Ile Val Gly Val Thr Ala Leu Gly
                260                 265                 270

Leu Leu Ile Ile Gly Val Val Asn Cys Val Ile Met Thr Gln Val Lys
            275                 280                 285

Lys Lys Pro Leu Cys Leu Gln Arg Glu Ala Lys Val Pro His Leu Pro
        290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
                340                 345                 350

Val Glu Ala Ser Gly Ala Gly Glu Ala Arg Ala Ser Thr Gly Ser Ser
            355                 360                 365

Asp Ser Ser Pro Gly Gly His Gly Thr Gln Val Asn Val Thr Cys Ile
        370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
                420                 425                 430

Gln Leu Glu Thr Pro Glu Thr Leu Leu Gly Ser Thr Glu Glu Lys Pro
            435                 440                 445

Leu Pro Leu Gly Val Pro Asp Ala Gly Met Lys Pro Ser
        450                 455                 460
```

PREVENTION OR TREATMENT OF HEMATOLOGIC MALIGNANCY RELAPSE USING A TNFR2 ANTAGONIST

BACKGROUND OF THE INVENTION

Allogeneic hematopoietic stem cell transplantation (AHCT) is a treatment of choice for several hematological malignancies, including leukemia and lymphoma. AHCT is often referred to as "bone-marrow transplantation" (hereafter designated as "BM"); stem cells can however be also collected from peripheral blood or from umbilical cord blood. After a myeloreductive conditioning associating high-dose chemotherapy+/−irradiation, patients receive a transplant containing hematopoietic stem cells from a healthy donor. This transplant comprises not only hematopoietic stem cells (HSC), which have the potential to reconstitute hematopoiesis for the long term, but also immunocompetent cells including mature Tcells. The therapeutic role of these donor Tcells is essential since they favor engraftment, promote peripheral Tcell reconstitution and, importantly, provide a graft-versus-leukemia/tumor (GVL) effect. Hence, in addition to the cytoreductive contribution of the conditioning, AHCT can be viewed as an allogeneic immune-based cell therapy of cancer (Ferrara et al, Lancet 2009). This is attested by the increased risk of hematologic malignancy relapse observed when alloreactivity is reduced or absent e.g. autograft, syngeneic twin graft or T cell depleted allogeneic transplantation. Another risk of this alloreactive effect is the life-threatening graft-versus-host disease (GVHD). GVHD is one of the major causes of morbidity and mortality following AHCT.

Alloreactive T cells represent approximately 5-10% of a normal T cell repertoire. When infused into an allogeneic recipient, these T cells do activate in response to host antigen presenting cells (APC), expand and differentiate into cytokine-producing and cytotoxic effectors cells that cause tissue damage on target organs. In order to prevent GVHD, grafted patients receive an immunosuppressive regimen but this treatment is only partially effective. During the 3 last decades, new strategies aiming at dissociating the deleterious effect of donor T cells while preserving their beneficial ones were intensively developed but with very limited success.

The inventors have previously demonstrated in experimental GVHD mouse models that $CD4^+CD25^{high}Foxp^{3+}$ thymus-derived regulatory T cells (Treg) depletion could intensify GVHD (Cohen et al. JEM 2002). Based on this observation, the inventors have successfully completed in 2010 the first worldwide clinical trial of Treg manipulation relying on ex vivo Treg depletion from donor lymphocyte infusions (DLI) through their CD25 constitutive expression, in order to improve the GVL effect in patients that relapsed after AHCT (Maury et al. Sci. Transl. Med. 2010). However, the procedure of ex vivo Treg depletion required a dedicated cell therapy unit allowing good manufacturing practice (GMP) compatible cell preparation. This limits the dissemination of this approach which also remains costly and time consuming.

By contrast, it has also been showed that cell therapy using Treg allows experimental GVHD to be efficiently prevented without hampering immune reconstitution or GVL activity. These pre-clinical models led to the development of clinical trials of Treg-based cell therapy with already very promising results. However, this approach of Treg collection and ex vivo expansion remains costly as well, and also difficult to develop under GMP-compliant procedures.

Treg are thus key target cells to modulate the allogeneic immune response in both ways. GVHD is a clinical setting particularly appropriate to finely tune the immune response by acting on Treg in order (i) either to prevent GVHD or (ii) to increase alloreactivity to improve the GVL effect. However, due to the difficulty to develop Treg-based cell therapy, it is critical to have alternative approaches for the prevention or treatment of hematologic malignancy relapse after AHCT.

Relapse hematologic malignancy occurs usually within the 6 months after AHCT and represents a significant therapeutic challenge. Patients in this setting are often young, without comorbidities and able to tolerate additional therapies: expectations are often still high. The approach to treatment depends on clinical variables (time to relapse, perceived sensitivity to additional cytotoxic therapy, disease stage), prior history of radiation therapy and the availability of an HLA-identical donor. Relapse may be due to graft failure due to an inadequate numbers of transplanted hematopoietic stem cell (HSC) or to the failure of adequate number of cells to survive. The barriers to engraftment include immunologic destruction of the graft, infectious agents, drug toxicity or a poor marrow microenvironment.

The occurrence of graft failure or rejection should be identified early and recognized as a serious and life-threatening process requiring intervention. Management consists of augmentation by growth factors without additional HSC infusions, infusions of HSC, a donor lymphocyte infusion (DLI) or the performance of a complete second AHCT. The objective is therefore to enhance GVL activity.

Thus, there is a need to find new approaches for prevention or treatment of hematologic malignancy relapse after AHCT and/or a treatment for enhancing GVL activity of an AHCT.

SUMMARY OF THE INVENTION

The inventors propose here to exacerbate alloreactivity for a powerful GVT activity to prevent or to treat hematological malignancy relapse after AHCT.

The invention relates to a TNFR2 antagonist for use in the prevention or treatment of hematologic malignancy relapse after allogeneic hematopoietic stem cell transplantation (AHCT) or after a treatment with lymphocytes, wherein said TNFR2 antagonist is to be administered to the subjects during or after the hematopoietic stem cell transplantation (HCT) or the treatment with lymphocytes.

The invention also relates to a TNFR2 antagonist for use in enhancing the graft versus leukemia activity (GVL activity) of an allogeneic hematopoietic stem cell transplantation (AHCT) or a treatment with lymphocytes wherein said TNFR2 antagonist is to be administered to the subjects during or after the hematopoietic stem cell transplantation (HCT) or the treatment with lymphocytes.

DETAILED DESCRIPTION OF THE INVENTION

The invention relates to a TNFR2 antagonist for use in the prevention or treatment of hematologic malignancy relapse after hematopoietic stem cell transplantation (HCT) or after a treatment with lymphocytes, wherein said TNFR2 antagonist is to be administered to the subjects during or after the allogeneic hematopoietic stem cell transplantation (AHCT) or the treatment with lymphocytes.

Unlike TNFR1, which has ubiquitous cellular expression, TNFR2 is expressed in a more limited manner, restricted primarily to subpopulations of T cells (in particular, Tregs), endothelial cells, and neurons. T regulatory cells (Tregs) are a small subset of T-lymphocytes with diverse clinical applications in transplantation, allergy, asthma, infectious diseases, GVHD, and autoimmunity. The Tregs can be used to suppress the abnormal immune response in patients in need thereof. Tregs are also known to be involved in immunotolerance in conditions such as cancer. Naturally occurring Tregs constitute only 1-5% of total CD4+ T cells in blood, and remain largely dormant until activated. In humans, Tregs are defined by co-expression of CD4+ and high expression of the interleukin-2 (IL-2) receptor alpha chain $CD25^{hi}$. Tregs also feature inducible levels of intracellular transcription factor Foxp3 and the expression of Foxp3 can be used to identify Tregs.

TNFR2 Antagonist

The term "Antagonist", as used herein, is used in the broadest sense, and includes any agent that partially or fully suppresses, inhibits, or neutralizes a biological activity of TNFR2 or TNFR2 signaling. Methods for identifying antagonists of TNFR2 can comprise contacting a TNFR2 with a candidate TNFR2 antagonist molecule and measuring a detectable change in one or more biological activities normally associated with the TNFR2. The TNFR2 antagonist that can be used in the invention can include agents, preferably selected from the group consisting of an anti-TNFR2 antibody, a peptide, a small molecule and a protein, preferably an anti-TNFR2 monoclonal antibody, that can bind to TNFR2 and partially or fully suppress TNFR2 signaling. The TNFR2 antagonist can be an agent that partially or fully inhibits the binding of TNF to TNFR2. The TNFR2 antagonist can be an agent that, when contacted with CD4+ T cells, can stimulate the expression of clAP but not the expression of TRAF2, TRAF3, or FOXP3. The TNFR2 antagonist can be a monoclonal antibody that binds TNFR2 (i.e. an anti-TNFR2 monoclonal antibody). There are two epitopes of TNFR2 to which the TNFR2 antagonist antibody can bind. The first epitope includes positions 48-67 (QTAQMCCSKCSPGQHAKVFC) of SEQ ID NO: 1 (amino acid sequence of human TNFR2). The second epitope includes position 135 (R) of SEQ ID NO: 1 (e.g., positions 135-153 (RLCAPLRKCRPGF) of SEQ ID NO: 1). For example, the anti-TNFR2 antagonist antibody (or TNFR2 antagonist antibody) can be any one of Clone MAB726 (R&D Systems, Inc.), Clone M1 (BD Biosciences), Clone LS-C11205 (LifeSpan BioSciences), Clone LS-C96330/Utr1 (LS-C96330) or Clone MA1-24723 (Invitrogen Antibodies). While each MAB726 and M1 binds the second epitope, an antibody of the invention may bind the first epitope or both epitopes. The TNFR2 antagonist antibody or antigen-binding fragment thereof can bind TNFR2 with a KD of less than about 50 nM (e.g., less than about 30 nM, less than about 20 nM, less than about 10 nM, less than about 5 nM, less than about 2 nM, less than about 1. nM, less than about 900 pM, less than about 800 pM, or less than about 700 pM). The TNFR2 antagonist antibody or antigen-binding fragment thereof can bind TNFR2 with a KD in the range of about 10 pM to about 50 nM (e.g., about 20 pM to about 30 nM, about 50 pM to about 20 nM, about 100 pM to about 5 nM, about 150 pM to about 1 nM, or about 200 pM to about 800 pM). The TNFR2 antagonist antibody avidity can be determined using methods known in the art (e.g., surface plasmon resonance. For example, MAB 726 binds TNFR2 with a KD of 621 pM (determined by surface plasmon resonance (Pioneer SensiQ®, Oklahoma City, Okla.)).

The table below discloses the references of commercially available anti-TNFR2 monoclonal antibodies.

| Provider | Reference | Clone rerefence | Isotype | Publication disclosing the antibody |
|---|---|---|---|---|
| LifeSpan BioSciences | LS-C11205-100 | 2/220 | IgG2a | |
| Invitrogen Antibodies | MA1-24723 | 22221, 311 | IgG2a | PNAS 105: 13644 (2008) |
| R&D Systems | MAB726-100 | 22210 | IgG1 | J. Immunol., 2007; 179(6): 4239-48 |
| LifeSpan BioSciences | LS-C96330-200 | Utr1 | IgG1 | Blood. 1994 Oct. 15; 84(8): 2506-14. |

The term "antibody," as used herein, includes whole antibodies or immunoglobulins and any antigen-binding fragment or single chains thereof. Antibodies, as used herein, can be mammalian (e.g., human or mouse), humanized, chimeric, recombinant, synthetically produced, or naturally isolated. For example, the antibody can be a monoclonal antibody, a polyclonal antibody, human antibody, a humanized antibody, a bispecific antibody, a monovalent antibody, a chimeric antibody, or camelidae-like antibody. The antibody can have any of the following isotypes: IgG IgM, IgA, IgD, or IgE.

An anti-TNFR2 antagonist antibody may be generated using techniques which are conventional in the art. Methods of producing antibodies include immunising a mammal (e.g. mouse, rat, rabbit, horse, goat, sheep, camel, llama or monkey) with a target polypeptide or a peptide fragment of the target. Antibodies may be obtained from immunised animals using any of a variety of techniques known in the art, and screened, preferably using binding of antibody to antigen of interest. For instance, Western blotting techniques or immunoprecipitation may be used.

As an alternative or supplement to immunizing a mammal with a peptide, an anti-TNFR2 antagonist antibody may be obtained from a recombinantly produced library of expressed immunoglobulin variable domains, e.g. using lambda bacteriophages or filamentous bacteriophages which display functional immunoglobulin binding domains on their surfaces.

An anti-TNFR2 antagonist antibody may be selected for its ability to reduce or block TNFR2-mediated TNF signaling using techniques described in the art.

The TNFR2 antagonist can also be a TNF-a mutein that is capable of binding to TNFR2 and suppressing downstream signaling.

The term "TNF-a mutein", as used herein, refers to a polypeptide having an amino acid sequence that differs from the amino acid sequence of TNF-a by one or more amino acids, while retaining the ability to activate or inhibit TNFR2. For example, a TNF-a mutein may have an amino acid sequence with greater than 90% but less than 100% sequence identity relative to the amino acid sequence of a reference polypeptide (TNF-a).

Hematologic Malignancy Relapse

The term "relapse", as used herein, means that the tumor, which had shown a regression or stagnation, has resumed its development or, where appropriate, has metastasized.

Hematologic malignancies relapse that can be prevented or treated by administering the TNFR2 antagonist include relapse of one or more hematologic malignancies selected from the group consisting of acute myeloid leukemia (AML), myeloproliferative disorders, myelodysplasia (also known as myelodysplastic syndromes) and lymphoproliferative syndromes. Myeloproliferative disorders include polycythemia vera (PV), essential thrombocythemia (ET), myelofibrosis and chronic myelogenous leukemia (CML). Myelodysplastic syndromes include refractory anemia (RA), refractory anemia with ring sideroblasts (RARS), refractory anemia with excess blasts (RAEB), refractory anemia with excess blasts in transformation (RAEB-T) and chronic myelomonocytic leukemia. Lymphoproliferative syndromes include follicular lymphoma, chronic lymphocytic leukemia, acute lymphoblastic leukemia (ALL), hairy cell leukemia, B-cell lymphomas, T-cell lymphomas, multiple myeloma, Waldenstrom's macroglobulinemia, Wiskott-Aldrich syndrome, post-transplant lymphoproliferative disorder, autoimmune lymphoproliferative syndrome (ALPS) and lymphoid interstitial pneumonia. In a preferred embodiment, the hematologic malignancy is acute leukemia (AML or ALL).

Patient

The intended patient is a human being, regardless of age and gender. The patient has a hematologic malignancy. Among the hematologic malignancy, there may be mentioned acute myeloid leukemia, myeloproliferative disorders, myelodysplasia and lymphoproliferative syndromes, these disorders or syndromes being as defined above. In a preferred embodiment, the hematologic malignancy is acute leukemia (AML or ALL).

The patient has undergone an AHCT, and eventually has undergone a donor lymphocyte infusion (DLI). Preferably, the prior allotransplantation of HSC is derived from a familial donor, preferably geno-identical HLA, or from a non-related volunteer donor. This may be a transplantation with myeloablative or non-myeloablative conditioning, and it may have been T-depleted or not.

The intended patient may exhibit a molecular, cytogenetic or cytological relapse of the hematologic malignancy regardless of the date thereof after the transplantation.

The relapse criteria are generally defined according to the hematologic malignancy.

For example, for an acute leukemia (AML or ALL) and myelodysplasia:
Persistence of blood blasts and/or excess of medullary blasts (>5%), and/or
In case of a residual disease that can be analyzed from the molecular point of view: absence of reduction (by at least one log) of the molecular signal relative to the pre-ILD point (Preexisting Interstitial Lung Disease point), or reduction followed by an increase (of at least one log relative to the nadir).
In case of a residual disease that can be analyzed from the cytogenetic point of view (conventional or FISH): absence of a reduction (of at least 50%) of the number of mitosis carrying the abnormality or abnormalities, or reduction followed by an increase (of at least 50% relative to the nadir).

For a myeloma:
Stability or increase in the monoclonal peak relative to the pre-ILD point.
Light chain myeloma: stability or increase in the parameters capable of being evaluated (bone lesions, proteinuria, medullary plasmocyte infiltration).
Absence of a reduction, reduction followed a rise, or appearance of a plasmocytic tumor.

For a chronic lymphoid leukemia, lymphomas:
Stability or increase of the clone (evaluated by flow cytometry, molecular biology) relative to the pre-ILD point.
Absence of a reduction or a reduction followed a rise in the tumor syndrome (evaluated from a clinical and/or radiological point of view) relative to the pre-ILD point.

Administration of the TNFR2 Antagonist

In one embodiment, the TNFR2 antagonist (e.g., anti-TNFR2 antagonist antibody) may be administered to a patient for the prevention of hematologic malignancy relapse. In this embodiment, the TNFR2 antagonist (e.g., anti-TNFR2 antagonist antibody) may be administered to a patient less than 2 hours after the ASCT, preferably less than 1 hour, preferably simultaneously to the ASCT.

In another embodiment, the TNFR2 antagonist (e.g., anti-TNFR2 antagonist antibody) may be administered to a patient for the treatment of hematologic malignancy relapse. In this embodiment, the TNFR2 antagonist (e.g., anti-TNFR2 antagonist antibody) may be administered to a patient after diagnosis with a hematologic malignancy relapse.

Generally, the TNFR2 antagonist can be administered in any medically useful form, preferably in the form of a pharmaceutical composition. For example, preparing such a pharmaceutical composition may include the addition of compounds, e.g., adjuvants, preservatives, carriers, excipients, diluents, anti-bacterial or anti-mycotic agents, anti-inflammatory agents, and/or anti-cancer agents, where appropriate. The TNFR2 antagonist (e.g., anti-TNFR2 antagonist antibody) or pharmaceutical composition of the invention can be administered intravenously, intramuscularly, orally, by inhalation, parenterally, intraperitoneally, intraarterially, transdermally, sublingually, nasally, subcutaneously or intrathecally, and they are formulated, as appropriate, depending on the chosen route of administration.

The daily dosage of the TNFR2 antagonist (e.g. an anti-TNFR2 antagonist) may be varied over a wide range from 0.01 to 1,000 mg of a TNFR2 antagonist (e.g. an anti-TNFR2 antagonist) per adult per day (e.g. 0.01, 0.05, 0.1, 0.5, 1.0, 2.5, 5.0, 10.0, 15.0, 25.0, 50.0, 100, 250 and 500 mg of a TNFR2 antagonist for the symptomatic adjustment of the dosage to the patient to be treated. But generally ranges from about 0.01 mg to about 500 mg of a TNFR2 antagonist, typically from 1 mg to about 100 mg of a TNFR2 antagonist. Preferably, TNFR2 antagonist is to be administered in an amount from 0.0002 mg/kg to about 20 mg/kg of body weight per day, especially from about 0.001 mg/kg to 10 mg/kg of body weight per day, for example from 3 mg/kg to 7 mg/kg of body weight per day.

The TNFR2 antagonist (e.g., anti-TNFR2 antagonist antibody) may be administered to a patient in one or more doses (e.g., 2, 3, 4, 5, 6, 7, 8, 9, or 10 or more doses). If more than one dose is to be administered, the doses may be administered via the same mode of administration (e.g., intravenous administration) or by different modes of administration (e.g., intravenous and intramuscular administration). The patient may also be administered different doses at different times. For example, the patient may be administered a higher initial dose and lower subsequent doses over the course of treatment or vice versa.

The TNFR2 antagonist (e.g., anti-TNFR2 antagonist antibody) may be administered daily, weekly, monthly, or yearly. For example, a dose of the TNFR2 antagonist may be administered twice daily, biweekly, bi-annually, tri-annually, or quarterly. The dose of the TNFR2 antagonist may be determined by a skilled physician upon consideration of a subject's clinical symptoms and/or physical condition (e.g., weight, sex, height, and severity of the proliferative or infectious disease). The TNFR2 antagonist may be administered intravenously, intramuscularly, orally, by inhalation, parenterally, intraperitoneally, intraarterially, transdermally, sublingually, nasally, subcutaneously or intrathecally, preferably intravenously.

The TNFR2 antagonist used in the present invention may be administered individually, or in combination with or concurrently with one or more other compounds known to prevent or treat a hematologic malignancy relapse after AHCT.

Enhancing the Graft-Versus-Leukemia-Activity (GVL Activity)

In a second aspect, the invention provides a TNFR2 antagonist for use in enhancing the graft-versus-leukemia-activity (GVL activity) of an allogeneic hematopoietic stem cell transplantation (AHCT) or a treatment with lymphocytes, wherein said TNFR2 antagonist is to be administered to the subjects during or after the allogeneic hematopoietic stem cell transplantation (AHCT) or the treatment with lymphocytes.

The term "enhancing" as used herein refers to a change in state from a first to a second state, where the first state is the GVL activity prior to the administration of the TNFR2 antagonist, and the second state is the GVL activity after administration of the TNFR2 antagonist where the GVL activity of the second state is improved as compared to the first state as a result of the administration of the TNFR2 antagonist.

The TNFR2 antagonist is selected from the group consisting of an anti-TNFR2 antibody, a peptide, a small molecule and a protein, preferably an anti-TNFR2 monoclonal antibody, as detailed above in "TNFR2 antagonist".

The hematologic malignancy is selected from the group consisting of acute myeloid leukemia, myeloproliferative disorders, myelodysplasia (also known as myelodysplastic syndromes) and lymphoproliferative syndromes, preferably acute leukemia (AML or ALL), as detailed above in "hematologic malignancy relapse".

In one embodiment, the TNFR2 antagonist (e.g., anti-TNFR2 antagonist antibody) may be administered to a patient less than 2 hours after the ASCT, preferably less than 1 hour, preferably simultaneously to the ASCT. This means that the administration takes place less than 2 hours after the allogeneic hematopoietic stem cell transplantation (AHCT), preferably less than 1 hour, more preferably simultaneously to AHCT.

In another embodiment, the TNFR2 antagonist (e.g., anti-TNFR2 antagonist antibody) may be administered to a patient after diagnosis with a hematologic malignancy relapse. This means that the administration takes place after diagnosis with a hematologic malignancy relapse.

The daily dosage of the TNFR2 antagonist (e.g. an anti-TNFR2 antagonist) may be varied over a wide range from 0.01 to 1,000 mg of a TNFR2 antagonist (e.g. an anti-TNFR2 antagonist) per adult per day (e.g. 0.01, 0.05, 0.1, 0.5, 1.0, 2.5, 5.0, 10.0, 15.0, 25.0, 50.0, 100, 250 and 500 mg of a TNFR2 antagonist for the symptomatic adjustment of the dosage to the patient to be treated. But generally ranges from about 0.01 mg to about 500 mg of a TNFR2 antagonist, typically from 1 mg to about 100 mg of a TNFR2 antagonist. Preferably, TNFR2 antagonist is to be administered in an amount from 0.0002 mg/kg to about 20 mg/kg of body weight per day, especially from about 0.001 mg/kg to 10 mg/kg of body weight per day, for example from 3 mg/kg to 7 mg/kg of body weight per day.

The TNFR2 antagonist used in the present invention may be administered individually, or in combination with or concurrently with one or more other compounds known to enhance GVL activity.

The present invention also provides a method for treating hematologic malignancy comprising the steps of:
  Performing to a human in need thereof an allogeneic hematopoietic stem cell transplantation (AHCT) or administering lymphocytes;
  administering an effective amount of TNFR2 antagonist; said TNFR2 antagonist is to be administered to the subjects during or after the allogeneic hematopoietic stem cell transplantation (AHCT) or the treatment with lymphocytes.

The present invention also provides a method for treating hematologic malignancy relapse after allogeneic hematopoietic stem cell transplantation (AHCT) or after a treatment with lymphocytes comprising administering an effective amount of TNFR2 antagonist, said TNFR2 antagonist is to be administered to the subjects during or after the allogeneic hematopoietic stem cell transplantation (AHCT) or the treatment with lymphocytes.

FIGURES

FIG. 1 is a set of graphs showing that TNFα/TNFR2 disruption using anti-TNFR2 blocking mAb abolishes the protective effect of Treg after AHCT (A and B): [B6×C3H]F1 female mice underwent TBI (Total Body Irradiation) followed by transplantation with B6 BM (Bone Marrow) cells plus T cells or with B6 BM cells plus T cells supplemented with HY-Tregs. HY peptide was administered at day 0, 1, 3 and 6 and mice were treated or not with blocking anti-TNFR2 mAb administered at day, 0, 2 and 4. The experiment was performed twice and the resulting survival (A) and clinical score (B) data were pooled and compared among the three groups of mice. (C and D) Experimental groups consisted of mice grafted with B6 BM cells plus T cells treated or not with anti-TNFR2 administered on days, 0, 2 and 4. The experiment was performed twice and the resulting survival (C) and clinical score data (D) were pooled. Mice were sacrificed in case of weight loss>30% of initial weight or maximal clinical grade (i.e. 5/5). Kaplan-Meier survival curves were compared using log-rank test. For analysis of GVHD clinical grading curves, Area Under Curve (AUC) was calculated for each mouse then T-test or one-way ANOVA with post-Hoc analysis were performed depending on number of comparatives. ns: non-significant; *: P<0.05; : p<0.01; *: p<0.001.

Figure 2:
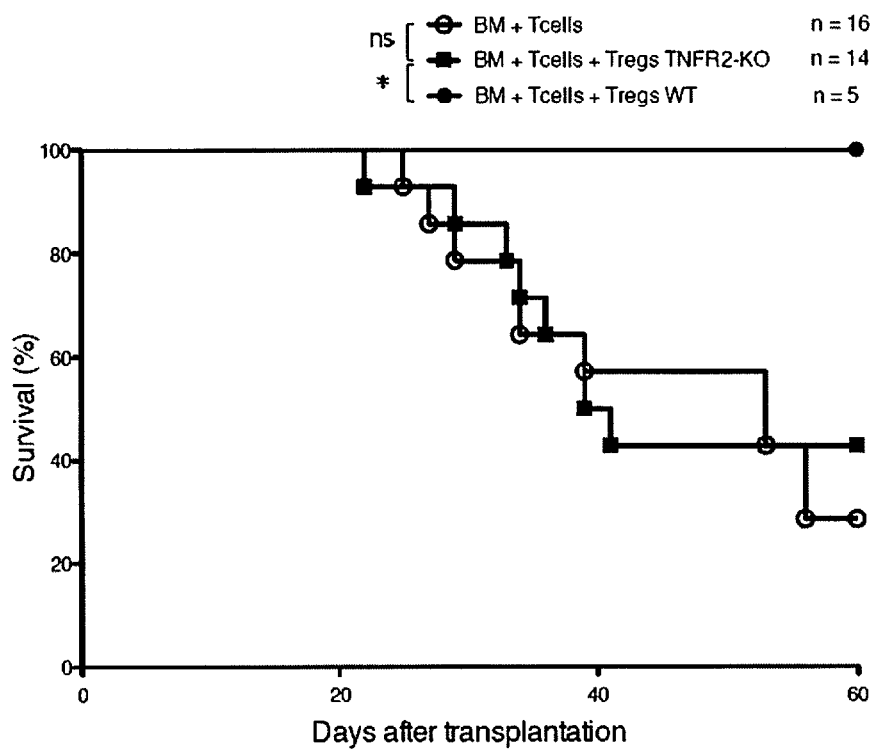
Figure 2:
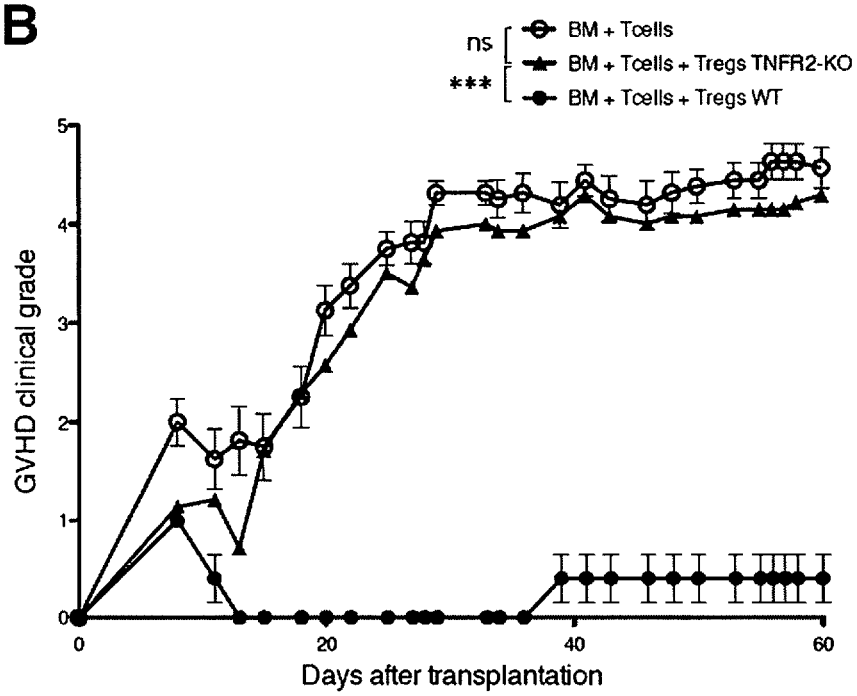

FIG. 2 is a set of graphs showing that TNFα/TNFR2 disruption using TNFR2-KO Tregs abolishes the protective effect of Treg after AHCT. [B6×C3H]F1 female mice underwent TBI followed by transplantation with B6 BM cells plus T cells or with B6 BM cells plus T cells supplemented with HY-Tregs produced from WT B6 or from TNFR2 deficient mice in order to prevent GVHD. HY peptide was administered on days 0, 1, 3 and 6. The experiment was performed twice and the resulting survival and clinical score data were pooled. (A) Kaplan-Meier survival curves and (B) curves of evolution of GVHD clinical score over time were compared between the three groups of mice. ns: non-significant; *: $p<0.05$; : $p<0.01$; *: $p<0.001$.

Figure 3:
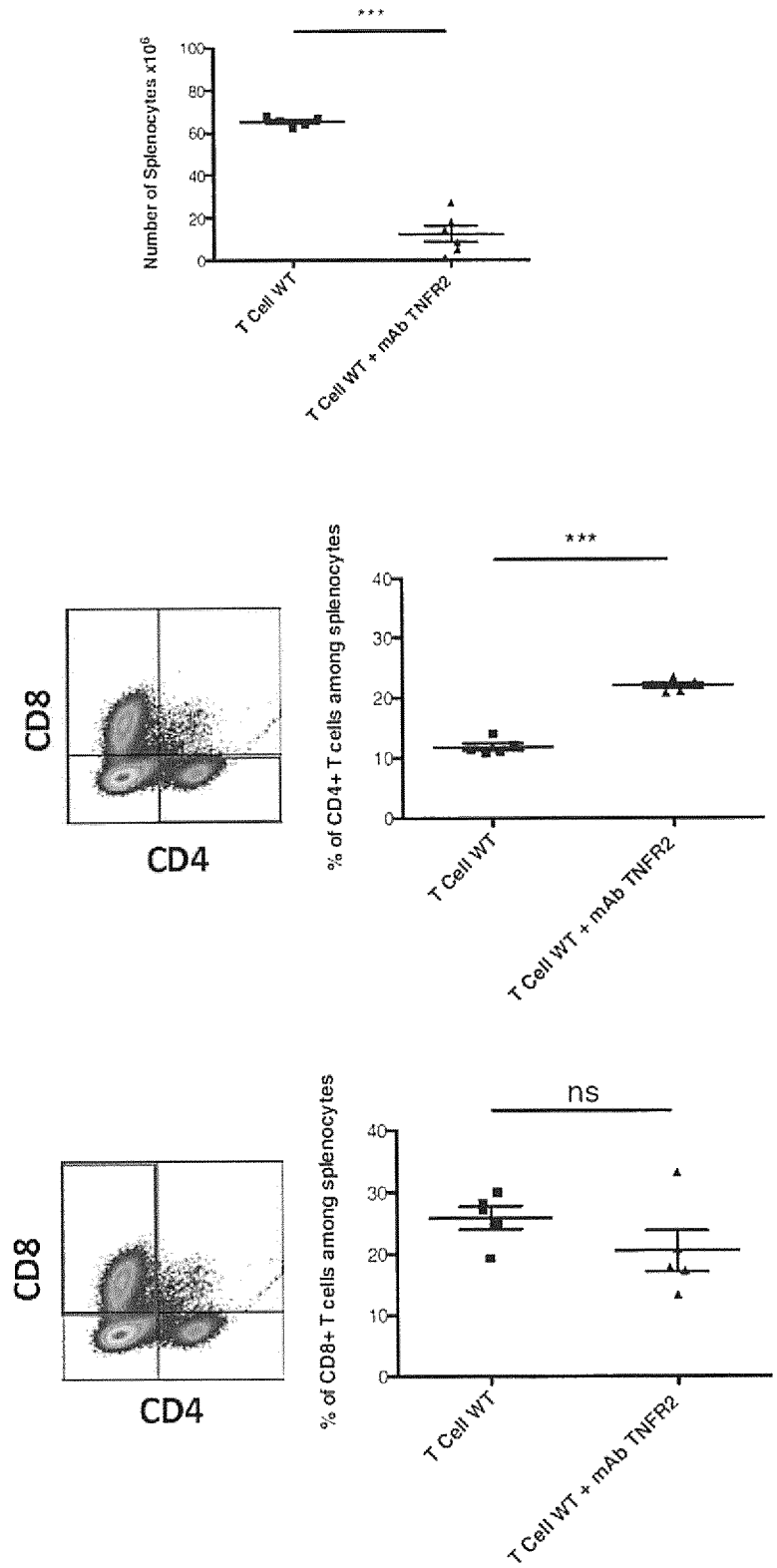
Figure 3:
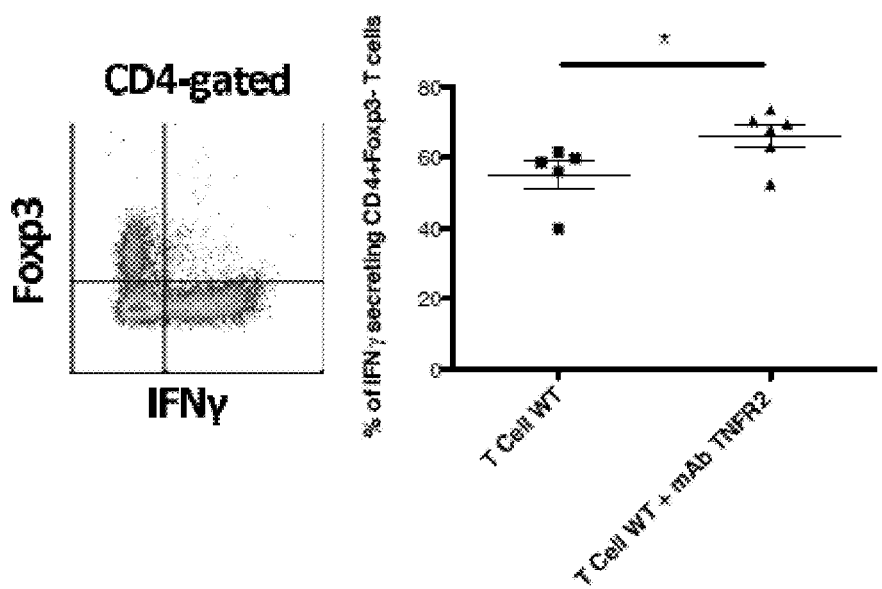
Figure 3:
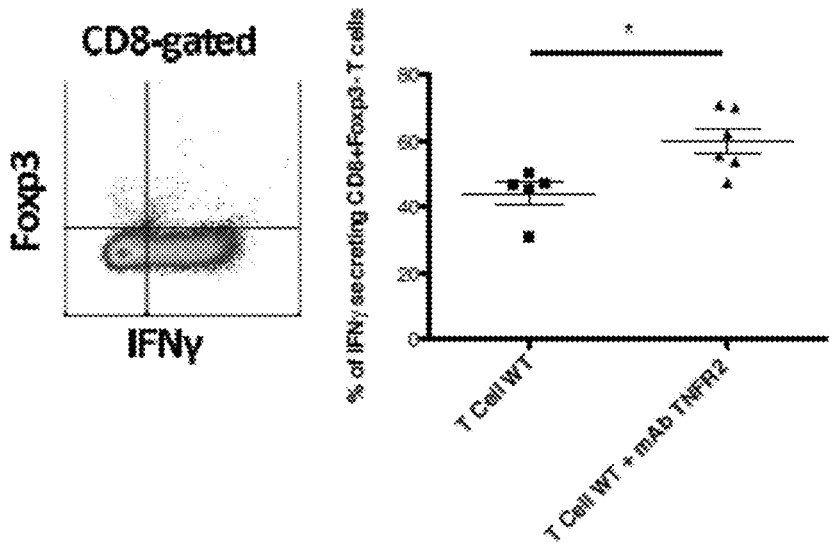
Figure 3:
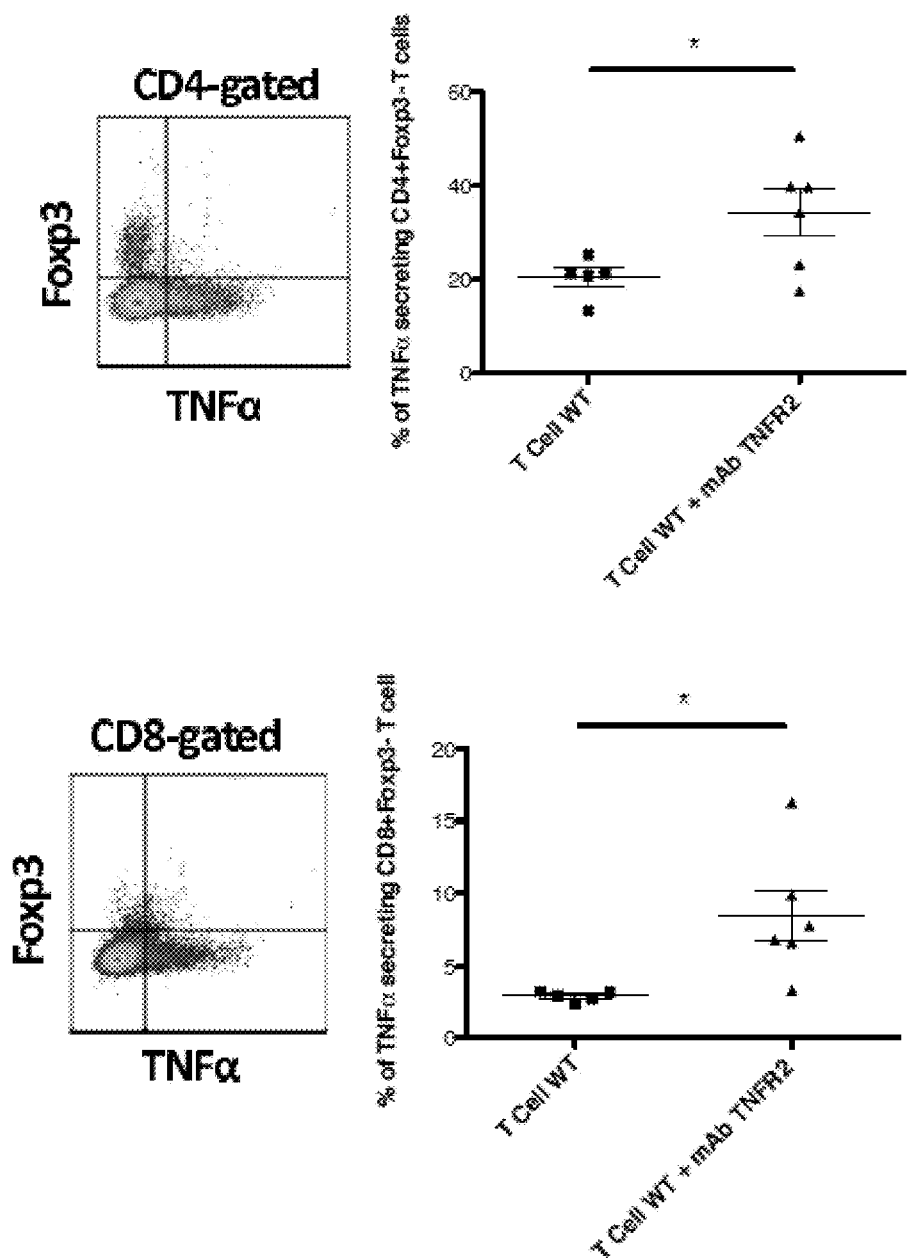

FIG. 3 is a set of graphs showing that TNFα/TNFR2 disruption using anti-TNFR2 blocking mAb increases inflammatory cytokine production by donor CD4 and CD8 T cells. [B6×C3H]F1 female mice underwent TBI followed by transplantation with B6 BM cells plus T cells treated or not blocking anti-TNFR2 mAb administered at day, 0, 2 and 4. Mice were sacrificed and donor $CD4^+$ and $CD8^+$ T cells were analyzed at day 14 post-transplantation in the spleen of grafted animals. Mean absolute numbers of splenocytes and percentage of $CD4^+$ and $CD8^+$ donor T cells are determined (A) as well as intracellular IFNγ (B) and TNFα (C) production. Each plot represents a mouse; T-test analysis was performed to compare anti-TNFR2 mAb effect on T cells. ns: non-significant; *: $p<0.05$; : $p<0.01$; *: $p<0.001$.

Figure 4:
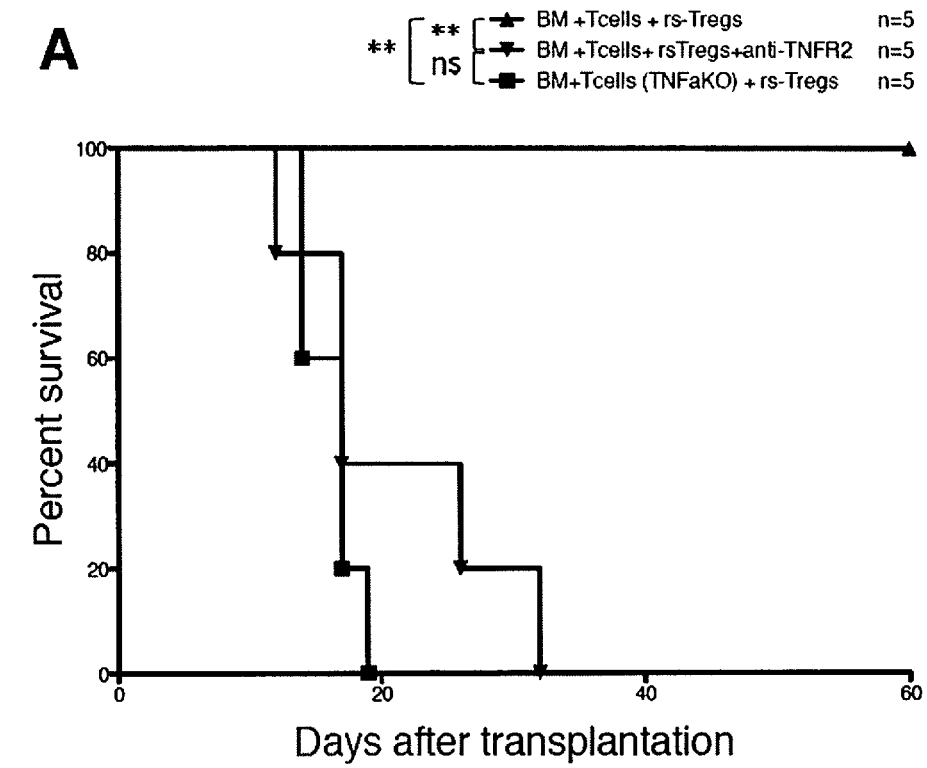
Figure 4:
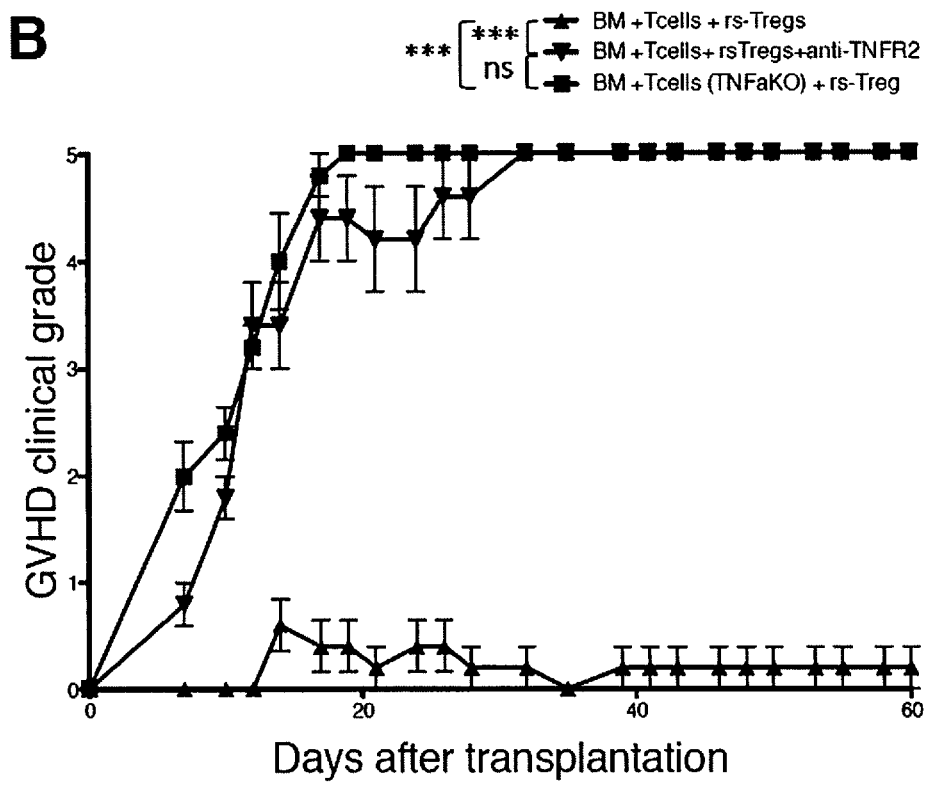

FIG. 4 is a set of graphs showing that TNFα/TNFR2 disruption and its effect on GVHD does not depend on the antigen specificity of therapeutic Tregs. (A and B): [B6× C3H]F1 female mice underwent TBI followed by transplantation with (i) B6 BM cells plus $2\times10^6$ T cells or (ii) with B6 BM cells plus $2\times10^6$ T cells supplemented with $2\times10^6$ rs-Tregs or (iii) BM cells plus $2\times10^6$ T cells collected from TNFα-deficient mice supplemented with $2\times10^6$ rs-Tregs. HY peptide was administered at day 0, 1, 3 and 6 and mice were treated or not with blocking anti-TNFR2 mAb administered at day, 0, 2 and 4. The resulting survival (A) and clinical score (B) data were compared among the three groups of mice. Mice were sacrificed in case of weight loss>30% of initial weight or maximal clinical grade (i.e. 5/5). Kaplan-Meier survival curves were compared using log-rank test. For analysis of GVHD clinical grading curves, Area Under Curve (AUC) was calculated for each mouse then one-way ANOVA with post-Hoc analysis was performed. ns: non-significant; *: $p<0.05$; : $p<0.01$; *: $p<0.001$.

Figure 5:
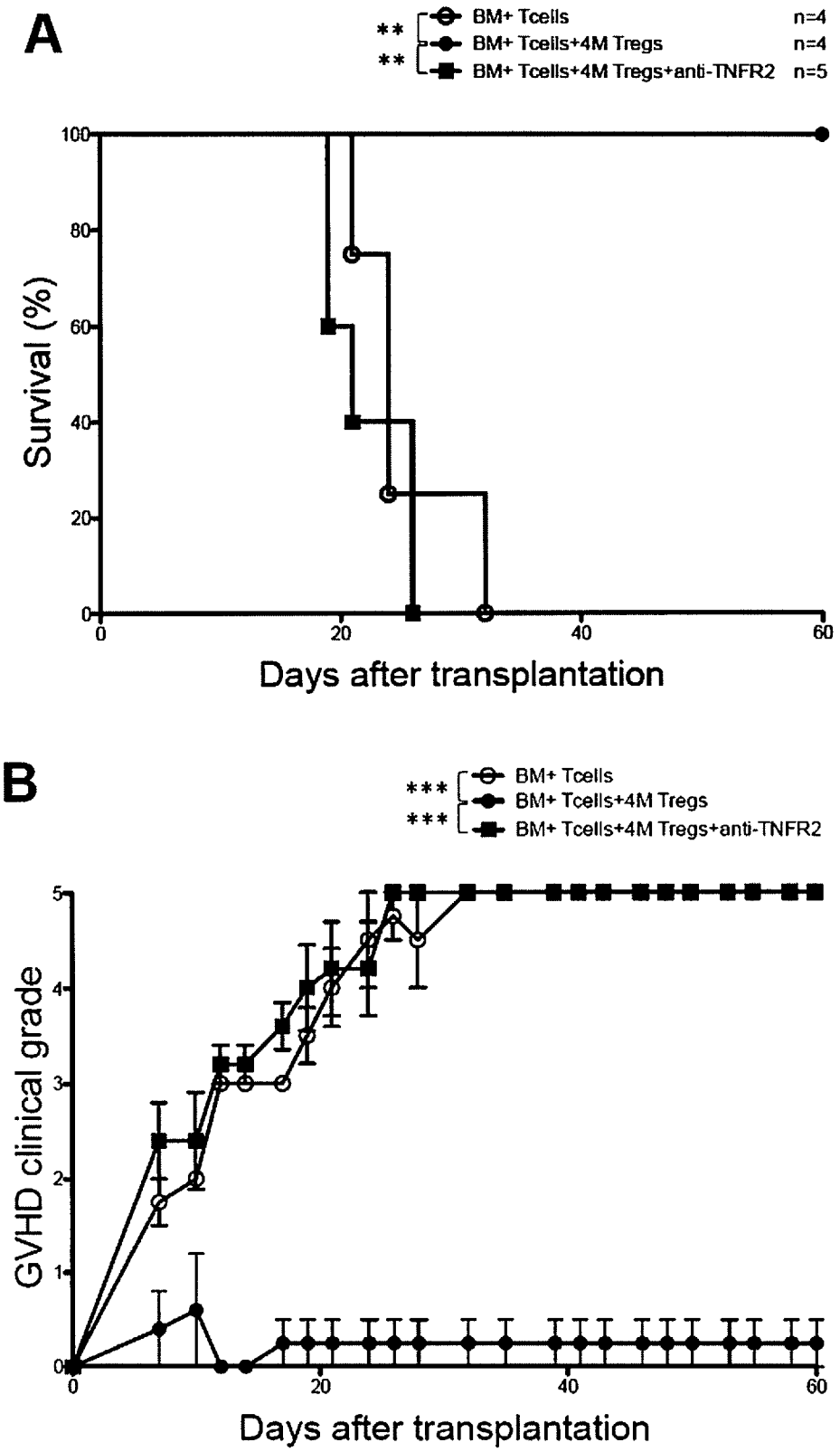

FIG. 5 is a set of graphs showing that TNFα/TNFR2 disruption and its effect on GVHD do not depend on the Treg/Tconv ratio.

(A and B): [B6×C3H]F1 female mice underwent TBI followed by transplantation with B6 BM cells plus T cells or with B6 BM cells plus $2\times10^6$ Tcells supplemented with $4\times10^6$ HY-Tregs. HY peptide was administered at day 0, 1, 3 and 6 and mice were treated or not with anti-TNFR2 administered at day, 0, 2 and 4. The resulting survival (A) and clinical score (B) data were compared among the three groups of mice. Mice were sacrificed in case of weight loss>30% of initial weight or maximal clinical grade (i.e. 5/5). Kaplan-Meier survival curves were compared using log-rank test. For analysis of GVHD clinical grading curves, Area Under Curve (AUC) was calculated for each mouse then oneway ANOVA with post-Hoc analysis was performed. ns: non-significant; *: $p<0.05$; : $p<0.01$; *: $p<0.001$.

Figure 6:
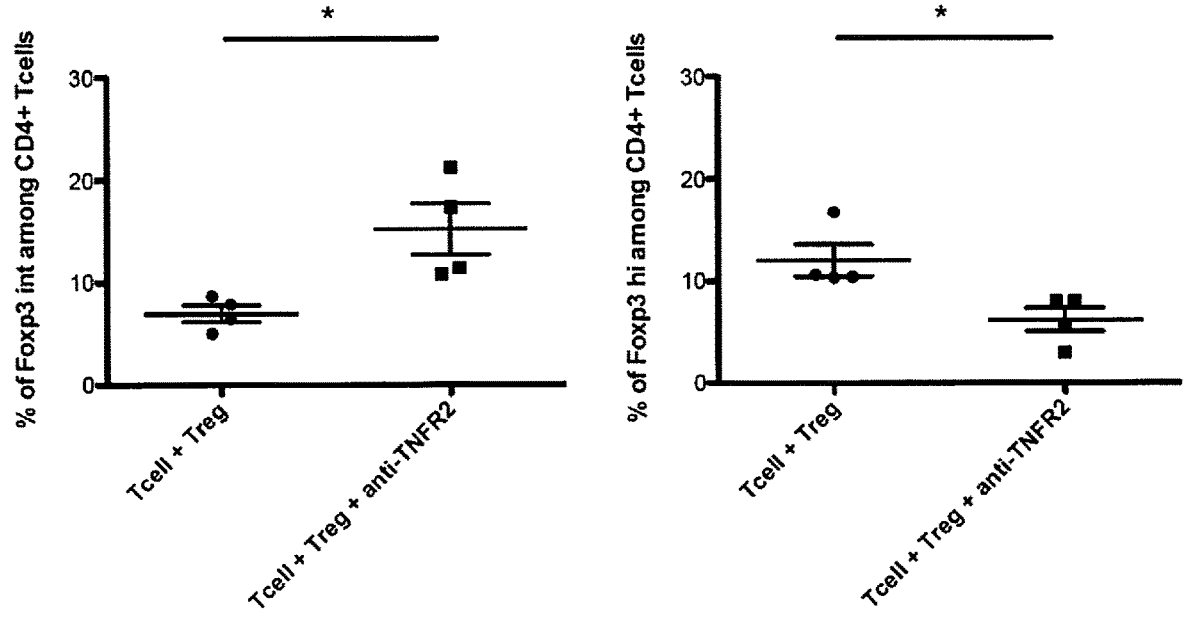
Figure 6:
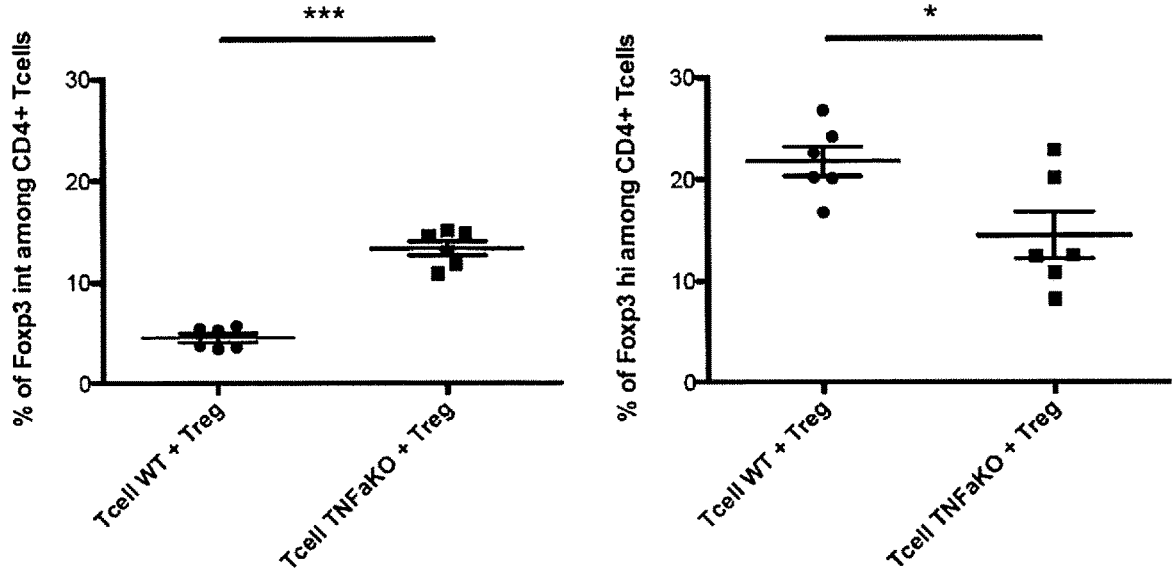

FIG. 6 is a set of graphs showing that blockade of the TNFα/TNFR2 interaction reduces Foxp3 expression in Tregs used to prevent GVHD.

GVHD experiments were reproduced using (up) blocking anti-TNF mAb treatment or (down) T cells collected from TNFα-deficient mice. Splenocytes from grafted animals were harvested at day 13 post-transplantation and enriched in $CD4^+$ and $CD8^+$ cells through positive magnetic selection using large selection columns (Miltenyi Biotec). Cells were then gated on $CD4^+$ cells. MFI values are represented as ratio of the measured value for each sample to the mean value of the control group (i.e. the group of mice receiving BM cells plus T cells and T reg cells). We have normalized the Mean Fluorescence Intensity (MFI) values with Tcell+ Treg control group. Then, we compared $Foxp3^{high}$, $Foxp3^{int}$ and $Foxp3^{low}$ expression on $CD4^+$ cells. We used unpaired, two-tailed Student's t tests for generation of p-values. ns: non-significant; *: $p<0.05$; : $p<0.01$; *: $p<0.001$; ****: $p<0.0001$.

Figure 7:
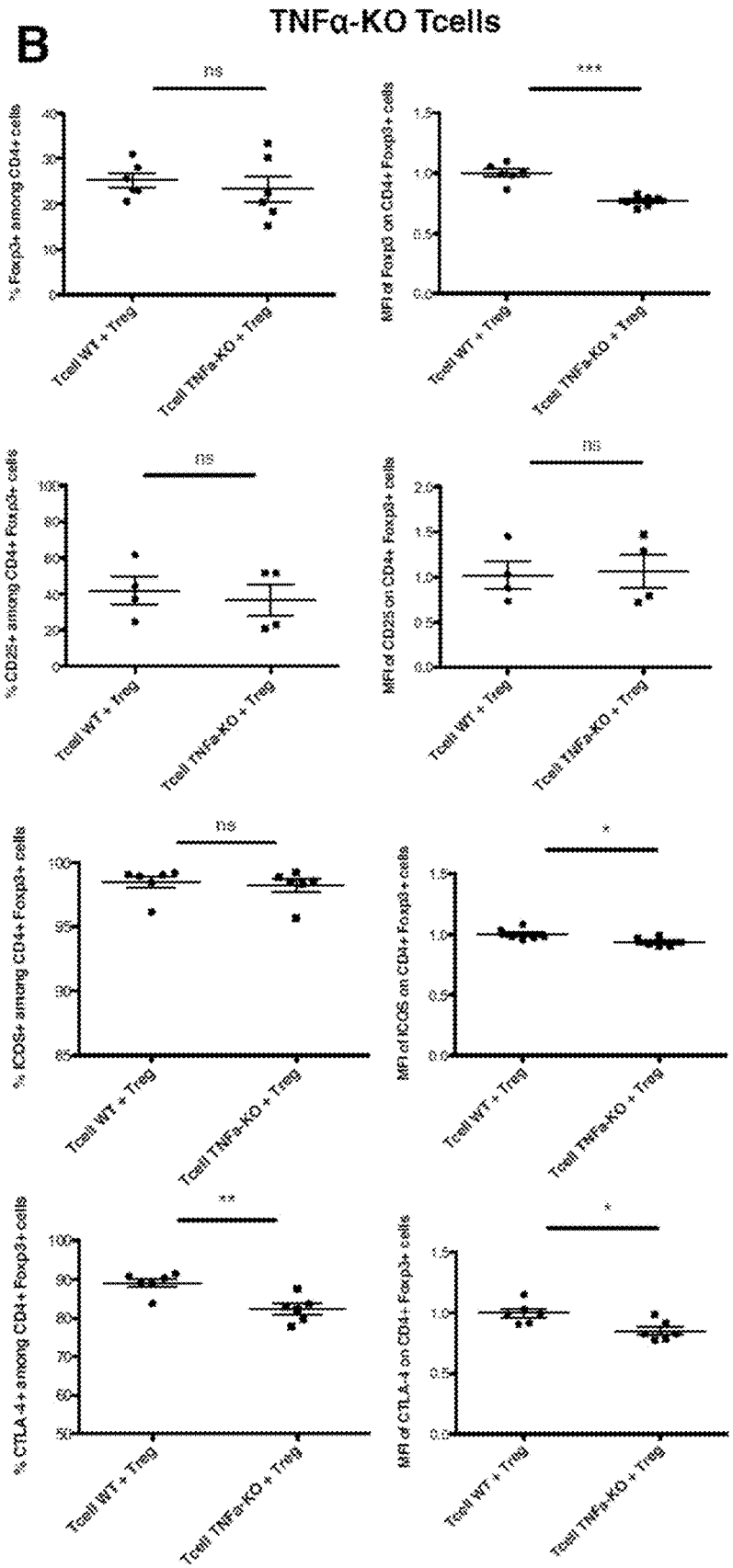

FIG. 7 is a set of graphs showing that blockade of the TNFα/TNFR2 interaction reduces Foxp3 and activation markers expressions in Tregs used to prevent GVHD. GVHD experiments were reproduced using (A) blocking anti-TNFR2 mAb treatment or (B) T cells collected from TNFα-deficient mice. Splenocytes from grafted animals were harvested at day 13 post-transplantation and enriched in $CD4^+$ and $CD8^+$ cells through positive magnetic selection using large selection columns (Miltenyi Biotec). Depending on the marker evaluated, Tregs were stained with CD4-FITC, CD4-APC or CD4-Vioblue, Foxp3-PE-Cy5 or Foxp3-V450, and CD25-PE-Cy7, ICOS-PE, CTLA4-biotin. Intracellular Foxp3 staining was performed using the Foxp3 staining buffer set from eBioscience. Cells were gated on CD4+ Foxp3+ cells except for the percentage of Foxp3 (up), which is gated on $CD4^+$ cells. For each marker, the strategy of gating is indicated on the left of the figure. Each dot represents a single mouse. For each group of mice, horizontal lines represent mean value and SEM. MFI values are represented as ratio of the measured value for each sample to the mean value of the control group (i.e. the group of mice receiving BM cells plus Tcells and Treg cells. We have normalized the Mean Fluorescence Intensity (MFI) values with Tcell+Treg control group. Then we used unpaired, two-tailed Student's t tests for generation of p-values. ns: non-significant; *: $p<0.05$; : $p<0.01$; *: $p<0.001$; ****: $p<0.0001$.

Figure 8:
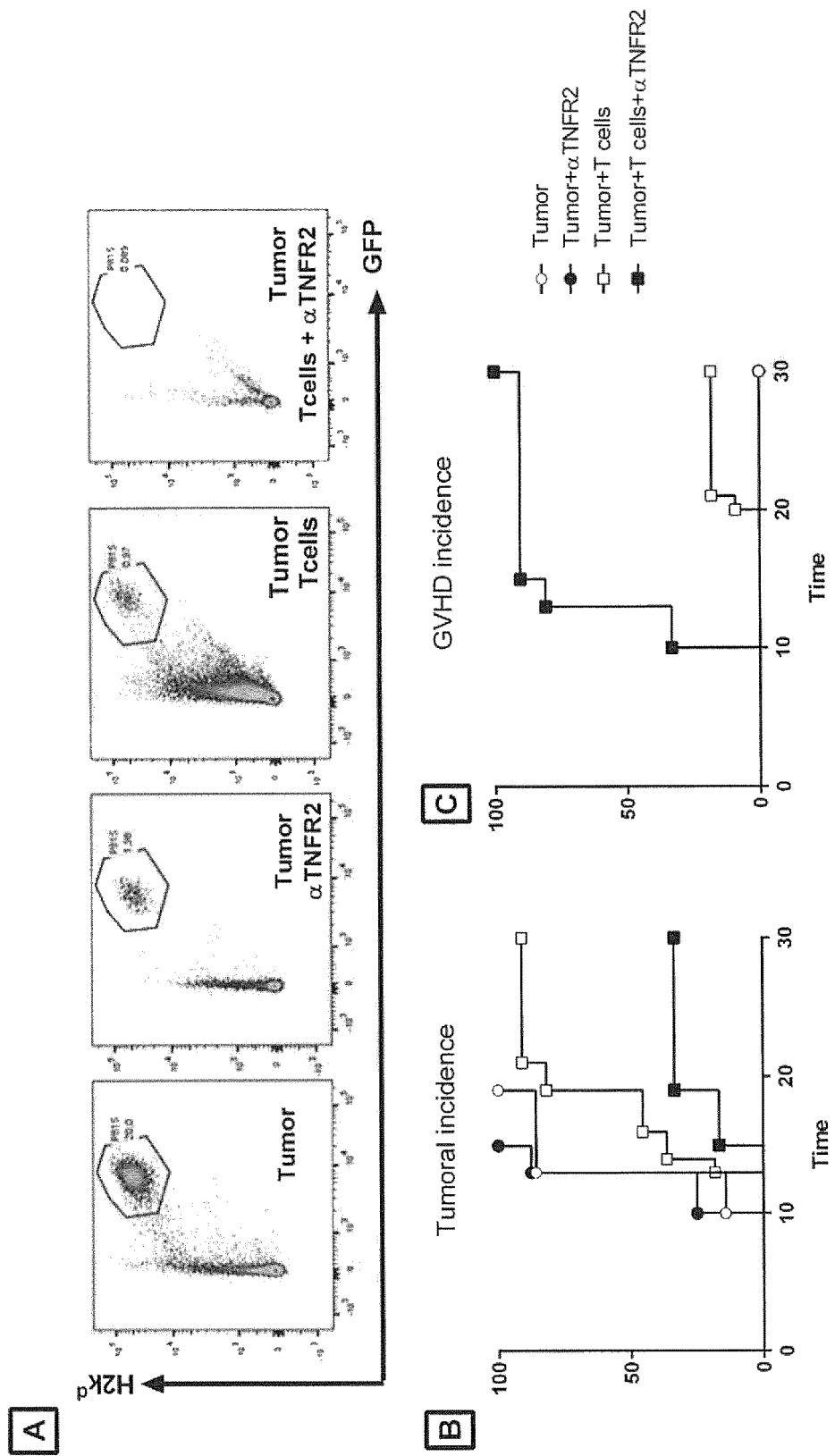

FIG. 8 is a set of graphs showing:
FIG. 8A: P815 characterization in blood sample of grafted animals at day 12. 12 days after bone marrow transplantation and P815 administration. p815 cells were detected in blood of grafted mice
FIG. 8B: Tumor incidence in alloSCT grafted mice. Efficiency of anti-TNFR2 blocking mAb treatment was T cells dependent because there is no difference between treated and untreated group when mice were transplanted without T cells.
FIG. 8C: GVHD incidence in alloSCT grafted mice. The GVL effect has linked to GVHD incidence.

EXAMPLES

Materials and Method

Mice
Wild-type C57BL/6 (66 H-2b) and B6C3HF1 (H-2kxb) mice were purchased from Harlan Laboratories (Gannat, France) and Charles River Laboratories (Saint-Germain-Nuelles, France). TNFR2–/– (TNFRs1b–/–) mice (i.e. mice KO for TNFR2) were purchased from the Jackson Laboratory (Bar Harbor, Me., USA). All mice were on a C57BL/6 background. Mice were housed under specific pathogen-free conditions. All experimental protocols were approved by the local ethics committee (authorization N° 11/12/12-5B) and are in compliance with European Union guidelines.

Treg Preparation

Treg were prepared as previously described (Martin G H, Gregoire S, Landau D A, et al. In vivo activation of transferred regulatory T cells specific for third-party exogenous antigen controls GVH disease in mice. Eur J Immunol. 2013; 43(9):2263-2272). Briefly, spleens and lymph nodes from C57BL/6 female mice were collected and mechanically dilacerated. Cell suspension was stained with biotin-coupled anti-CD25 monoclonal antibody (mAb) (7D4, BD Biosciences, San Diego, Calif., USA), followed by anti-biotin microbeads (Miltenyi Biotec, Paris, France) and CD25+ cells were positively selected through magnetic large selection column (Miltenyi Biotec). Selected cells were stained with the following mAbs: CD4-FITC (eBioscience, San Diego, Calif., USA), CD62L-PE (eBioscience), CD25-biotin (BD Biosciences) and streptavidin-PE-Cy5 (eBioscience). $CD4^+$ $CD25^{high}$ $CD62L^{high}$ cells (i.e. Treg cells) were then sorted using a MoFlo Legacy (Beckman Coulter, Villepinte, France), with a purity of 99%.

For HY-Treg preparation, purified Treg cells were cultured for 3 to 4 weeks in the presence of recombinant murine IL-2 (long/mL; PeproTech, Neuilly-sur-Seine, France) and weekly stimulated with $CD8^+$ dendritic cells (DCs) previously loaded with the HY peptide (10 µg/mL, N-15-S, NY, PolyPeptide, Strasbourg, France) in the presence of GM-CSF (20 ng/mL; PeproTech). CD8+ DCs were isolated from splenocytes of C57BL/6 mice, as previously described (Maury S, Lemoine F M, Hicheri Y, et al. CD4+CD25+ regulatory T cell depletion improves the graft-versus-tumor effect of donor lymphocytes after allogeneic hematopoietic stem cell transplantation. *Sci Transl/Med.* 2010;2(41): 41ra52). For recipient-specific (rs)Treg preparation, purified Treg cells were cultured for 3 to 4 weeks in the presence of recombinant murine IL-2 and weekly stimulated with irradiated total splenocytes from C3H female mice, as previously described (Di Ianni M, Falzetti F, Carotti A, et al. Tregs prevent GVHD -and promote immune reconstitution in HLA-haploidentical transplantation. *Blood.* 2011;117 (14):3921-3928—and—Gaidot A, Landau D A, Martin G H, et al. Immune reconstitution is preserved in hematopoietic stem cell transplant co-administered with regulatory T cells for GVHD prevention. *Blood.* 2011;117 (10):2975-2983).

GVHD and Transplantation Models

Eight-to-twelve weeks-old recipient B6C3HF1 female mice received a 10 Gy irradiation followed by retro-orbital infusion of 10.106 bone marrow cells+2.106 $CD3^+$ T cells, with or without HY-Treg cells in a 1:1 ratio (i.e. 2.106 HY-Treg cells). Bone marrow and T cell suspensions were prepared using leg bones and splenocytes respectively, as previously described (Cohen J L; Boyer O, Salomon B et al. Blood 1997). All infused cells (Bone Marrow, T lymphocytes T and Treg) were isolated from female C57BL/6 mice (semi-allogeneic model). As recipient and donor mice were females, HY-Treg cells were activated in vivo by repeated retro-orbital infusions of 100 g of the HY peptide (at Day 0, Day 1, Day 3 and Day 6), as previously described (Martin G H, Gregoire S, Landau D A, et al. In vivo activation of transferred regulatory T cells specific for third-party exogenous antigen controls GVH disease in mice. Eur J Immunol. 2013;43(9):2263-2272). For rs-Treg experiments, mice were transferred with rs-Treg cells in a 1:1 ratio.

Antibody Treatment

Anti-TNFR2 (TR75-54.7) mAb was purchased from Bio X Cell (West Lebanon, N.H., USA). Recipient mice were treated with 3 intra-peritoneal injections of 500 g of the antibody on days 0, 2 and 4. GVHD clinical grading GVHD clinical score was calculated 2 to 3 times per week. Each of the 5 following parameters was scored 0 (if absent) or 1 (if present): weight loss>10% of initial weight, hunching posture, skin lesions, dull fur and diarrhea. Dead mice received a global score of 5. Mice were sacrificed in case of weight loss>30% of initial weight or maximal clinical grade (i.e. 5/5).

It has to be understood from the examples that a high GVL activity is correlated with a high GVHD clinical score. Therefore, the increase of GVHD clinical score reflects an enhancement of the GVL activity and a GVHD protection reflects a decrease of GVL activity.

Histopathological Examination.

Livers, lungs, skin, small and large bowels samples were preserved in Bouin's fixative and embedded in paraffin. For these organs, 5-µm-thick sections were stained with hematoxylin and eosin for histological examination as previously described (Trenado A, Sudres M, Tang Q, et al. Ex Vivo-Expanded CD4+ CD25+ Immunoregulatory T Cells Prevent Graft-versus-Host-Disease by Inhibiting Activation/Differentiation of Pathogenic T Cells. *J Immunol.* 2006;176(2): 1266-1273). Briefly, one pathologist analyzed slides in a blinded fashion to assess the intensity of GVHD. GVHD lesions in each sample were scored according to a semi-quantitative scoring system described by Hill et al. with minor modifications (Hill G R, Cooke K R, Teshima T, et al. Interleukin-11 promotes T cell polarization and prevents acute graft-versus-host disease after allogeneic bone marrow transplantation. *J Clin Invest.* 1998; 102(1): 115-123).

Flow Cytometry

Two weeks after transplantation (i.e. at Day 13, Day 0 being the date of transplantation and Treg cell injection), recipient mice were sacrificed and their spleens collected. Because of the low proportion of Treg cells among splenocytes and the low overall spleen cellularity at Day 13, cell suspensions obtained for each spleen were enriched in $CD4^+$ and $CD8^+$ cells after labeling with anti-CD4 and anti-CD8 microbeads (Miltenyi Biotec) and positive magnetic selection through large selection columns (Miltenyi Biotec). Selected cells were then stained with the following mAbs: CD4-FITC, CD4-APC and CD4-Vioblue (Miltenyi Biotec), Foxp3-PE-Cy5 and Foxp3-V450 (eBioscience), CD25-PE-Cy7 (eBioscience), CD62L-PE (eBioscience), ICOS-PE (eBioscience), CTLA4-biotin (followed by streptavidin-PE-Cy7; eBioscience), IFNγ-PE (Miltenyi Biotec), TNFα-FITC (Miltenyi Biotec), CD8α-FITC (eBioscience). Intracellular Foxp3 staining was performed according to the manufacturer's instructions, using the Foxp3 staining buffer set from eBioscience. For intracellular cytokine staining, cells were re-stimulated with 1 µg/mL PMA (Sigma Aldrich, Saint Quentin Fallavier, France) and 0.5 µg/mL Ionomicyn (Sigma Aldrich) for 5 h, in the presence of GolgiPlug (1 µL/mL; BD Biosciences). Events were acquired on a FACSCanto II flow cytometer (BD Biosciences) and analyzed using FlowJo software vX.0.7 (FlowJo, LLC, Ashland, Oreg., USA).

Statistical Analysis

Prism (GraphPad Software) was used for statistical analysis. Kaplan meier survival curves were compared using log-rank test. For analysis of GVHD clinical grading curves, Area under curve (AUC) were calculated for each mouse then T-test or one-way ANOVA with post-Hoc analysis were performed depending on number of comparatives. For cytometry analysis, we have normalized the Mean fluorescence intensity (MFI) values with T cell+Treg cell control group. Then we used unpaired, two-tailed Student's t tests for generation of p-values.

Example 1

TNFR2 Plays a Pivotal Role in Treg-Mediated Prevention of GVHD and Anti-TNFR2 Antagonist Enhancement of GVL To assess the role of TNF on GVHD and GVL by Treg administration, we first used our recently described model in which the disease was prevented by transfer in females recipients of donor Tregs specific for the exogenous (i.e non-donor, non-recipient) HY antigen at time of AHCT, followed by their in vivo re-activation by HY peptide immunization (Martin G H, Gregoire S, Landau D A, et al. In vivo activation of transferred regulatory T cells specific for third-party exogenous antigen controls GVH disease in mice. Eur J Immunol. 2013;43(9):2263-2272). In a semi-allogeneic condition C57BL/6>[B6×C3H]F1 of bone marrow transplantation, GVHD protection at 1/1 Treg/Tconv ratio strictly depends on HY immunization.

We evaluated the role of TNFR2 in Treg-mediated GVHD and GVL using a anti-TNFR2 antagonist mAb (hereafter "blocking anti-TNFR2 mAb") (FIGS. 1A and B). Mice transferred with Tconvs developed severe GVHD that was prevented by the co-transfer of HY-Tregs. The GVHD protection of Treg administration was fully abolished in mice that were treated with the blocking anti-TNFR2 mAb. These latter mice displayed high clinical GVHD scores and decreased survival, as compared to HY-Treg-treated control mice. The decrease of GVHD protection suggests that blocking anti-TNFR2 mAb can enhance the GVL activity of AHCT.

In order to assess whether a higher Treg:Tconv ratio could overcome the effect due to TNFR2 blockade, we reproduced the same experiment doubling the number of HY-Treg infused in recipient mice (2/1 Treg/Tconv ratio). Even with this increased numbers of therapeutic Tregs, blocking TNFR2 fully abolished the Treg-dependent GVHD protection (FIG. 5). This demonstrates the specificity of blocking anti-TNFR2 mAb to enhance the GVL activity of AHCT.

We then used TNFR2-deficient HY-specific Tregs, obtained from TNFR2KO mice, to confirm that the Treg control of GVHD and GVL by TNF was mediated by TNFR2 expression by Tregs. Whereas TNFR2-sufficient control Tregs fully protected from GVHD, TNFR2-deficient Tregs completely failed to protect mice from GVHD (FIG. 2). Survival of the mice and clinical scores of GVHD were identical in mice receiving donor Tconvs alone and mice receiving donor Tconvs and TNFR2-deficient Tregs. These results suggest that TNFR2 is key for GVL activity and that blocking anti-TNFR2 mAb is sufficient to enhance GVL activity.

We then assessed the role of TNFR2 in Treg-mediated protection in another transplant setting. Tregs naturally present in the donor T-cell inoculum were present in sufficient number to attenuate GVHD since their depletion accelerated the disease (Cohen J L, Trenado A, Vasey D, Klatzmann D, Salomon B L. CD4(+)CD25(+) immunoregulatory T Cells: new therapeutics for graft-versus-host disease. *J Exp Med*. 2002;196(3):401-406). Here, we observed that blocking TNFR2 with blocking anti-TNFR2 mAb led to a similar high GVHD clinical score, which reflects an increase of GVL activity. Indeed, in mice grafted with bone marrow cells (AHCT) and whole T cells containing Tregs at physiological level, administration of the blocking anti-TNFR2 mAb induced an accelerated GVHD (FIGS. 1 C and D). These results suggest that blocking anti-TNFR2 mAb can enhance the GVL activity of AHCT. The number of splenocytes collected at day 14 importantly varied between the two groups of mice. Whereas spleens of mice grafted with T cells contain 65.4×106±2.2 cells, this number fell sharply to 12.3×106±9.6 in mice treated with blocking anti-TNFR2 mAb, probably reflecting an accelerated GVHD and an increased GVL. We next evaluated the effect of blocking TNFR2 mAb on cytokine production in the spleen of mice developing GVHD after transfer of WT donor T cells. Mice treated with the blocking anti-TNFR2 mAb had an increase in IFNγ and TNFα-production in both CD4 and CD8 donor T cells (FIG. 3). In order to reinforce the robustness of our observations, we used a third transplant setting consisting in infusing Tregs that were rendered specific for recipient-type allo-Ag, (namely rs-Treg) instead of HY-Treg to prevent GVHD. Whereas GVHD was prevented by rs-Treg administration, this protective effect was fully abolished when using blocking anti-TNFR2 mAb (FIG. 4). Thus, using 2 different approaches (anti-TNFR2 mAb and TNFR2-deficient Tregs) and different types of Tregs (Tregs of the T cell inoculum, therapeutic HY-Tregs or rs-Tregs), we demonstrate that the control of GVHD by Tregs is TNFR2 dependent. Thus, we have demonstrated that blocking anti-TNFR2 mAb can accelerate GVHD, suggesting that blocking anti-TNFR2 mAb can enhance GVL activity of an allogeneic hematopoietic stem cell transplantation (AHCT) or a treatment with lymphocytes.

Conclusion: The enhancement of GVL activity of AHCT could be mediated through TNFR2 expressed by Tregs. TNF-TNFR2 interaction is critical in the regulation of GVL activity by Tregs in AHCT performed either in routine or in clinical trials when therapeutic Tregs are injected. A TNFR2 antagonist can enhance the GVL activity of a AHCT or a treatment with lymphocytes.

Example 2

After AHCT, TNF/TNFR2 Blockade Reduces Foxp3 and Activation Markers Expression on Tregs To analyze by what mechanism the control of GVHD by Tregs and enhancement of the GVL activity depends on TNF/TNFR2 interaction, we measured the proportion and activation markers of Tregs in the spleen collected at day 13 in mice grafted with HY-Tregs and either WT Tcells and treated with blocking anti-TNFR2 mAb or TNF-deficient Tcells. First, the expression level of Foxp3 was significantly reduced when TNF/TNFR2 interaction was inhibited in both settings, whereas Treg proportions remained unchanged (FIG. 7 A, B). This lower Foxp3 expression among whole Tregs was characterized by a reduced proportion of Foxp3$^{high}$ expressing cells and an increased proportion of Foxp3$^{int}$ expressing cells in both experimental models (FIG. 6). A likely explanation would be that, in the absence of TNFR2 signaling in Tregs, Foxp3 would be down-modulated, suggesting that TNF stabilized Foxp3 expression in Tregs. In the same line, in the absence of TNFR2 signaling, Treg could be less stable and could convert into pro-inflammatory T cells.

We further analyzed the expression of CD25, the a chain of the IL-2 receptor constitutively expressed at the Treg cell surface membrane. We observed a dramatic decrease of the percentage of CD25+ cells and CD25 expression level among Tregs when blocking anti-TNFR2 mAb was administered to grafted mice. Since in experimental AHCT CD25 expression is up-regulated by IL-2, these results suggest that TNFα increased IL-2 responsiveness of Tregs in this context.

Finally, we evaluated the expression of ICOS and CTLA4, which are important molecules in Treg biology. In both models of inhibition of TNF/TNFR2 interaction (i.e. blocking anti-TNFR2 mAb or TNF-deficient Tcells), ICOS and CTLA-4 expressions were reduced compared to controls, with a more pronounced effect in mice treated with the blocking anti-TNFR2 mAb than mice grafted with TNFα-deficient T cells (FIG. 7), probably reflecting the more complete abrogation of TNF signaling in the presence of the monoclonal antibody.

Conclusion: TNF activates Treg via stabilization of Foxp3. The anti-TNFR2 reduces Foxp3 and thus blocks Treg and therefore increases alloreactivity. This suggests an enhancement of the GVL activity.

Example 3

Improved Anti-Tumor Effect of T Cells by Anti-TNFR2 Treatment

Eight to 12-week-old recipient B6D2F1 female mice received a 10 Gy irradiation followed by retro-orbital infusion of $5 \times 10^6$ bone marrow (BM) cells+$2 \times 10^4$ host type P815 (DBA/2-derived, H-2Dd, GFP) tumor cells, with (Tumour+T cells group; n=8) or without (Tumor group n=7) $1 \times 10^6$ T cells. BM and T cells were isolated from female C57BL/6 mice. Tumor (Tumor+TNFR2 group; n=11) and Tumor+Tcells group (Tumor+Tcells+·TNFR2 group; n=11) were treated with 3 intraperitoneal injections of 500 μg of the anti-TNFR2 blocking mAb (TR75-54.7) on days 0, 2, and 4.

The results are shown in FIG. 8: (FIG. 8A) P815 characterization in blood sample of grafted animals at day 12. Tumoral (FIG. 8B) and GVHD (FIG. 8C) incidence in alloSCT grafted mice.

Results: 12 days after bone marrow transplantation, p815 cells were detected in blood of grafted mice (FIG. 8A). When mice were transplanted with T cells then treated with the blocking anti-TNFR2 mAb, tumor incidence decrease compared to untreated mice (36% vs 91% respectively). Efficiency of blocking anti-TNFR2 mAb treatment was T cells dependent because there is no difference between treated and untreated group when mice were transplanted without T cells (FIG. 8B). As expected, this GVL effect has linked to GVHD incidence (FIG. 8C) and score (data no shown).

Conclusion: These results demonstrate that mice grafted with suboptimal numbers of T cells were capable to reject tumor cells when Treg functionality was abolished by anti-TNFR2 blocking treatment.

The invention claimed is:

1. Method for inhibiting hematologic malignancy relapse after allogeneic hematopoietic stem cell transplantation (AHCT) or after a treatment with lymphocytes, the method comprising administering an antagonistic anti-TNFR2 antibody to a subject in need thereof, wherein said antibody is administered to the subject during or after the allogeneic hematopoietic stem cell transplantation (AHCT) or the treatment with lymphocytes.

2. Method according to claim 1, wherein the hematologic malignancy is selected from the group consisting of acute myeloid leukemia, myeloproliferative disorders, myelodysplasia and lymphoproliferative syndromes.

3. Method according to claim 1, wherein the antagonistic anti-TNFR2 antibody is administered less than 2 hours after the allogeneic hematopoietic stem cell transplantation (AHCT) or after diagnosis with a hematologic malignancy relapse.

4. Method according to claim 1, wherein said antagonistic anti-TNFR2 antibody is administered in the form of a pharmaceutical composition.

5. Method according to claim 1, wherein said antagonistic anti-TNFR2 antibody is administered in an amount from 0.001 mg/kg to 10 mg/kg of body weight per day.

6. Method according to claim 1, wherein the hematologic malignancy is acute myeloid leukemia or acute lymphoblastic leukemia.

7. Method for enhancing graft versus leukemia activity (GVL activity) of an allogeneic hematopoietic stem cell transplantation (AHCT) or a treatment with lymphocytes, the method comprising administering an antagonistic anti-TNFR2 antibody to a subject in need thereof, wherein said antibody is administered during or after the allogeneic hematopoietic stem cell transplantation (AHCT) or the treatment with lymphocytes.

8. Method according to claim 7, wherein the hematologic malignancy is selected from the group consisting of acute myeloid leukemia, myeloproliferative disorders, myelodysplasia and lymphoproliferative syndromes.

9. Method according to claim 7, wherein the antagonistic anti-TNFR2 antibody is administered less than 2 hours after the allogeneic hematopoietic stem cell transplantation (AHCT) or after diagnosis with a hematologic malignancy relapse.

10. Method according to claim 7, wherein said antagonistic anti-TNFR2 antibody is administered in the form of a pharmaceutical composition.

11. Method according to claim 7, wherein said antagonistic anti-TNFR2 antibody is administered in an amount of from 0.001 mg/kg to 10 mg/kg of body weight per day.

12. Method according to claim 7, wherein the hematologic malignancy is acute myeloid leukemia or acute lymphoblastic leukemia.

13. Method for treating hematologic malignancy, the method comprising the steps of:
performing allogeneic hematopoietic stem cell transplantation (AHCT) or administering lymphocytes to a subject in need thereof;
administering to the subject an effective amount of an antagonistic anti-TNFR2 antibody during or after the allogeneic hematopoietic stem cell transplantation (AHCT) or the treatment with lymphocytes.

14. Method for treating hematologic malignancy relapse after allogeneic hematopoietic stem cell transplantation (AHCT) or after a treatment with lymphocytes, the method comprising administering an effective amount of an antagonistic anti-TNFR2 antibody to a subject in need thereof, wherein said antibody is administered during or after the allogeneic hematopoietic stem cell transplantation (AHCT) or the treatment with lymphocytes.

15. Method according to claim 14, wherein the hematologic malignancy is selected from the group consisting of acute myeloid leukemia, myeloproliferative disorders, myelodysplasia and lymphoproliferative syndromes.

16. Method according to claim 14, wherein the antagonistic anti-TNFR2 antibody is administered less than 2 hours after the allogeneic hematopoietic stem cell transplantation (AHCT) or after diagnosis with a hematologic malignancy relapse.

17. Method according to claim 14, wherein said antagonistic anti-TNFR2 antibody is administered in the form of a pharmaceutical composition.

18. Method according to claim 14, wherein said antagonistic anti-TNFR2 antibody is administered in an amount from 0.001 mg/kg to 10 mg/kg of body weight per day.

19. Method according to claim 14, wherein the hematologic malignancy is acute myeloid leukemia or acute lymphoblastic leukemia.

\* \* \* \* \*